(12) United States Patent
Akiba

(10) Patent No.: US 7,226,411 B2
(45) Date of Patent: Jun. 5, 2007

(54) VALVED PLUG FOR ENDOSCOPIC BIOPSY CHANNEL

(75) Inventor: Haruo Akiba, Saitama (JP)

(73) Assignee: Fujinon Corporation, Saitama (JP)

( * ) Notice: Subject to any disclaimer, the term of this patent is extended or adjusted under 35 U.S.C. 154(b) by 0 days.

(21) Appl. No.: 10/689,650

(22) Filed: Oct. 22, 2003

(65) Prior Publication Data
US 2004/0167379 A1 Aug. 26, 2004

(30) Foreign Application Priority Data
Oct. 23, 2002 (JP) .............................. 2002-308175

(51) Int. Cl.
*A61B 1/00* (2006.01)
(52) U.S. Cl. ...................... 600/154; 600/104; 600/121; 600/159; 604/167; 604/256
(58) Field of Classification Search ................ 600/154, 600/104, 121
See application file for complete search history.

(56) References Cited

U.S. PATENT DOCUMENTS 4,412,531 A * 11/1983 Chikashige ................. 600/104
4,649,904 A * 3/1987 Krauter et al. .............. 600/154
4,653,477 A * 3/1987 Akui et al. .................. 600/154
4,715,360 A * 12/1987 Akui et al. .................. 600/154
4,809,679 A * 3/1989 Shimonaka et al. ........ 600/154
5,863,286 A * 1/1999 Yabe et al. .................. 600/121
6,117,070 A * 9/2000 Akiba ......................... 600/154
6,165,124 A * 12/2000 Ouchi ......................... 600/154

* cited by examiner

*Primary Examiner*—Linda C. M. Dvorak
*Assistant Examiner*—Matthew J. Kasztejna
(74) *Attorney, Agent, or Firm*—Oblon, Spivak, McClelland, Maier & Neustadt, P.C.

(57) ABSTRACT

A valved plug to be fitted on a mouth piece at an inlet opening of an endoscopic biopsy channel. The plug as a whole is formed of a resilient material, and has, at the opposite ends of a foldable connecting strip or string, a generally tubular main body portion which is provided with a constricted portion in its axial passage, and a valved nesting piece which is adapted to be detachably coupled with the main body portion and provided with a normally closed slit valve axially in an aligned position relative to the constricted passage on the side of the main body portion. The main body portion is provided with an inward interlocking projection of a predetermined thickness at its outer end, for tight interlocking engagement with an interlocking groove which is provided on the side of the nesting piece in such a way as to grip the interlocking projection tightly in a compressed state.

6 Claims, 4 Drawing Sheets

F I G . 2
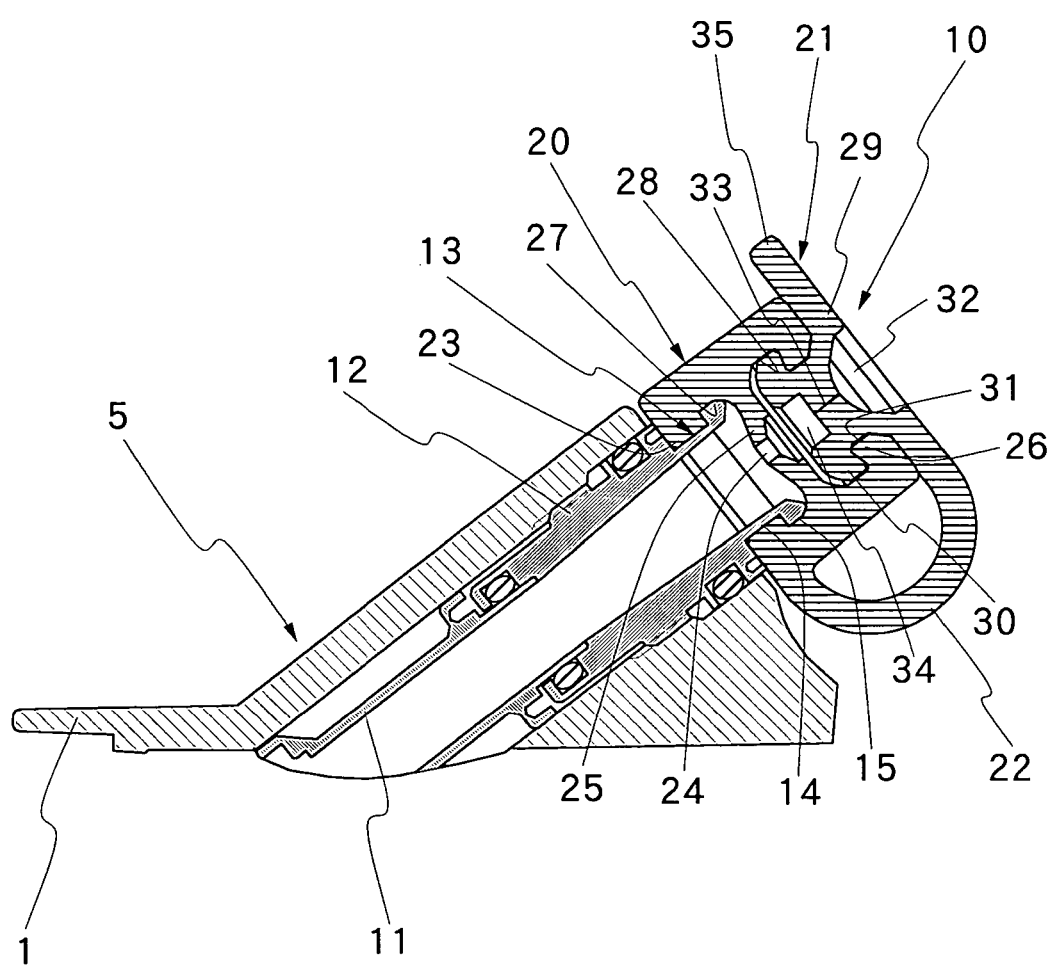

VALVED PLUG FOR ENDOSCOPIC BIOPSY CHANNEL

BACKGROUND OF THE INVENTION

1. Field of the Art

This invention relates to a valved plug for an endoscopic biopsy channel, and more particularly to a valved plug to be detachably fitted on a mouth piece at an entrance opening to a biopsy channel, which is provided on medical endoscopes for introduction of forceps or other biopsy and surgical instruments.

2. Prior Art

Generally, medical endoscopes which are introduced in a body cavity for examination or therapeutic purposes are largely constituted by a manipulating head assembly to be gripped in an operator's hand for manipulating of various control means, an insertion tube extended out on the front side of the manipulating head assembly, and a universal cable which is led out on the rear side of the manipulating head assembly for connection to a light source etc. Along with an endoscopic image pickup means, an illumination window or windows are provided in a casing of a tip end section at the fore distal end of the insertion tube to project illumination light toward an intracavitary site under examination.

For example, in case a diseased portion is spotted as a result of an endoscopic examination, it may become necessary to give a certain treatment to the diseased portion or to get tissue samples therefrom. Therefore, for this purpose, many endoscopes are provided with the so-called biopsy channel to permit introduction of forceps or other biopsy or surgical instruments therethrough. The biopsy channel is coextensively extended through the insertion tube of the endoscope toward an outlet opening which is provided on the casing of the distal tip end section along with the illumination and endoscopic image pickup means. A biopsy or surgical instrument is introduced into the biopsy channel through an inlet opening which is provided in the casing of the manipulating head assembly or at a joint portion of the insertion tube and the manipulating head assembly.

Partly because the pressure within a body cavity is higher than the atmospheric pressure and partly because the biopsy channel is also utilized as a suction passage, the inlet opening of the biopsy channel cannot be left in an open state. Therefore, it is the general practice to close the inlet opening of the biopsy channel with a plug, by fitting the plug on a mouth piece which is provided around the inlet opening. An instrument can be introduced into the biopsy channel without removing the plug from the mouth piece. Namely, the plug is provided with an on-off valve in its internal passage, which can be pushed open when an instrument is introduced into the biopsy channel. Nevertheless, since it is necessary to wash clean the interior of the biopsy channel each time after use, the plug is normally detachably fitted on the mouth piece of the biopsy channel.

Instrument to be introduced into a body cavity by way of the biopsy channel on an endoscope vary over a certain range in diameter, from forceps with relatively large outside diameters to narrow tubes with extremely small diameters. In other words, an endoscopic biopsy channel is used for introduction of instruments of diversified outside diameters. Ideally, the on-off valve to be provided in the plug should be capable of holding the circumference of an inserted instrument tightly in a sealed state. However, there have never been developed biopsy channel plugs which can maintain perfect air tightness around the circumference of various thick and narrow instruments which greatly differ in outside diameter, for example, perfect air tightness around a thick instrument which is almost as large as the diameter of the inlet opening of the biopsy channel as well as around a narrow instrument which is far smaller in diameter.

As for conventional biopsy channel plugs of the sort mentioned above, it has been widely known in the art to provide within a plug a constricted passage of a diameter smaller than the inlet opening of the biopsy channel and to provide a slit of a length equivalent with or larger than the diameter of the inlet opening in such a way that the slit is normally closed to maintain the inlet opening of the biopsy channel substantially in a hermetically closed state. The slit is pushed open upon introducing an instrument into the inlet opening of the biopsy channel. In the case of a narrow instrument, it is relatively easy to maintain air tightness because the slit is opened only in a small degree. On the contrary, when a thick instrument is introduced into the biopsy channel, the slit is opened wide to such a degree as to brake its air tightness. However, since the constricted passage is provided in addition to the slits, the thick instrument spreads the constricted passage radially outward as it is introduced into the biopsy channel, and walls of the constricted passage tightly fit around the inserted instrument to form a hermetical seal therearound. Therefore, while an instrument is introduced into a body cavity through the biopsy channel for a biopsy or surgical treatment, there is little possibility of body fluids flowing in a reverse direction and coming out through the inlet opening of the biopsy channel and depositing on the manipulating hand of the operator.

In this connection, there has been known in the art a plug construction which has the above-mentioned constricted passage and slit valve on one and same structure, for example, from Japanese Patent Publication H5-57848. More specifically, in the case of the Japanese Patent Publication just mentioned, the biopsy channel plug is composed of a tubular main body portion internally provided with a constricted passage and adapted to be fitted on a mouth piece at the entrance opening of a biopsy channel, and a lid member containing a slit as an on-off valve and connected with the main body portion through a flexibly foldable connecting strip. In use, firstly one end of the main body portion of the plug is fitted on the mouth piece of the biopsy channel entrance opening, and then the valved lid member is fitted in the other outer end of the main body portion.

The main body and the valved lid member of the plug are separably coupled with each other. In this regard, it is important for the main body portion and the valved lid member to be able to maintain hermetical tightness when coupled with each other. Therefore, in the case of the above-mentioned Japanese patent publication, an inwardly projecting annular brim is provided at the outer end of the main body portion. The annular brim is adapted to be trapped in an annular groove which is provided on the side of the valved lid member, when the valved lid member fitted into the main body portion of the plug. At this time, the inner periphery of the annular brim is abutted against the bottom of the annular groove to form a hermetical seal therebetween. The annular brim is formed in a thickness which is smaller than the width of the annular groove on the side of the lid member. Further, the lid member is formed with a flanged portion around its inner end to be fitted into the main body portion. On the other hand, an axially projecting annular ridge is provided on a partition wall around a constricted passage in such a way that the flange portion at the inner end of the lid member is gripped between the annular ridge and a lower surface of a wall portion which defines the annular trapping groove. Accordingly, the brim portion which is projected radially inward at the outer end of the main body portion is abutted against bottom surfaces and inner rising wall portions of the annular groove, but it is left out of contact with outer rising wall portions of the trapping groove.

By the way, among endoscopically inserting instruments of various sizes, an instrument of large diameter forcibly tends to spread the constricted passage radially outward upon introduction into the biopsy channel through the slit in the lid member of lid portion of the plug. At this time, the lid portion of the plug is pressed against the axially projecting ridge on the partition wall, and therefore it is retained in the coupled state without receiving adverse effects in this regard. However, when the thick instrument is extracted from the biopsy channel, the partition wall around the constricted passage is pulled and displaced in an upward direction. As a consequence, the lid portion of the plug is pushed by the axial ridge portion on the partition wall in a direction of separating same from the main body of the plug. The brim portion which is provided at the outer end of the main body portion is abutted against the inner rising wall portion of the annular groove on the side of the lid member, so that it acts to restrict movements of the lid portion. Namely, at the time an instrument is extracted from the biopsy channel, the force acting to separate the lid portion from the main body portion of the plug is sustained by the inwardly projecting brim portion which is provided at the outer end of the main body portion. Besides, since the top side of the brim portion in put in a free state and the axial ridge portion is located radially inward of the brim portion, the force acting to push up the lid portion through the brim portion is amplified by a degree which corresponds to a positional differential between the projected portion and the rim portion.

Therefore, the inwardly protruding brim portion at the outer end of the main body portion can be deformed into an outwardly bent form by repeated insertions and extractions of instruments, and as a result lid gripping force of the brim portion can be gradually deteriorated. In such a state, if an instrument is inserted into the biopsy channel through the plugged inlet opening and then abruptly extracted out of the plug, the lid portion of the plug can be unintentionally separated from the main body portion because the brim portion on the main body portion no longer has sufficient lid holding force. Further, as mentioned hereinbefore, the biopsy channel also serves for use as a suction passage. When a suction valve on the manipulating head assembly of the endoscope is operated for aspiration and then closed to end the aspiration, the flow of aspirate fluids within the biopsy channel is stopped and the pressure within the biopsy channel is elevated to a relatively high level. This elevated pressure acts on inner surfaces of the lid portion of the plug. Therefore, in case the lid holding force of the brim portion on the main body portion has deteriorated to a material degree, the lid portion of the plug can be pushed off the main body portion by the internal pressure of the biopsy channel. In such a case, a large amount of aspirate can flow out through the biopsy channel plug and scatter around the operator.

SUMMARY OF THE INVENTION

With the foregoing situations in view, it is an object of the present invention to provide a valved plug for an endoscopic biopsy channel, having a main body portion and a valved nesting piece at the opposite ends of a foldable connecting strip and being arranged in such a way that the valve nesting piece can be coupled with the main body portion without difficulties in particular but can be tightly and securely interlocked with to the main body portion once the plug is fitted on a mouth piece at an inlet opening of an instrument entrance passage leading to an endoscopic biopsy channel.

It is another object of the present invention to provide a valved plug for an endoscopic biopsy channel, which can suppress degradations in hermetical tightness of a slit in a valved nesting piece of the plug.

It is still another object of the present invention to provide a valved plug for an endoscopic biopsy channel, which can preclude possibilities of a valved nesting piece coming off a main body portion of the plug even when an inserted instrument is abruptly extracted out of the plug.

In accordance with the present invention, in order to achieve the above-stated objectives, there is provided a valved plug to be fitted on a mouth piece at an inlet opening of an instrument entrance passage leading to a biopsy channel of an endoscopic insertion tube, the plug being formed of a resilient material in its entirety and having, at opposite ends of a foldable connecting strip, a generally tubular main body portion internally formed with a constricted passage of a smaller diameter as compared with the inlet opening of the instrument entrance passage at an intermediate portion between outer and inner ends thereof, and a nesting piece adapted to be detachably and tightly coupled with the main body portion and having a normally closed slit valve in axial alignment with the constricted passage in the main body portion to permit insertion of an instrument therethrough, characterized in that: the main body portion is provided with an interlocking inward projection of a predetermined thickness at an outer end to be coupled with the nesting piece; and the nesting piece is composed of a circular body portion having a slit cut across a center region thereof, and an annular interlocking flange formed integrally with and on top of the circular body portion around the slit and spread radially outward to hang over circumferential edges of the circular body portion; the interlocking projection on the main body portion of the plug being adapted to be brought into engagement tightly with an interlocking groove formed between the flange portion and the circular body portion of the nesting piece and gripped in the interlocking groove in a compressed state when the nesting piece is coupled with the main body portion.

The plug as a whole is formed of a resilient material. In this regard, it is preferable to use silicon rubber or the like in consideration of degree of resiliency, strength and resistance to chemicals. The main body portion and the nesting piece of the plug are not necessarily required to be formed into one unitary structure. For example, the two parts may be formed separately by the use of different materials with properties best suited for the respective parts, and fixed to the opposite ends of a connecting strip or string afterwards. From the standpoint of simplifying the fabrication process, the main body portion, foldable connecting strip and valved nesting piece may be molded together as one integral structure.

The main body portion of the plug needs to be constructed in such a way that it can be detachably fitted on a mouth piece at an inlet opening of an entrance way leading to the biopsy channel. For this purpose, the main body portion is adapted to be fitted on and gripped by a rim portion which is provided around an outer end of the mouth piece. The constricted passage which is provided internally of the main body portion should have an open diameter which is large enough for permitting easy passage of a narrow instrument like a rubber tube but smaller than an outside diameter of relatively thick and stiff instrument like forceps.

On the other hand, the valved nesting piece is desired to have a body portion which is formed in a hemispherical cup-like shape, for using a concave hemispherical surface as a guide surface for instruments to be introduced into the biopsy channel. Accordingly, a slit is provided at a bottom portion of the concave side of the hemispherical body portion of the nesting piece. Although the slit is normally in the shape of a single straight slit, but it may be formed in other shapes, for example, in the shape of a crossed slit or the like. However, when no instrument is inserted, meeting edges of the slit should be closed tightly to each other to produce sealing effects.

Further, to facilitate passage of various instruments, preferably the valved nesting piece is formed of slippery or less frictional material or coated with a lubricant at the slit valve portion.

The above-mentioned interlocking projection is preferably in the form of an annular ledge which is projected radially inward at and from an outer end of the tubular main body portion of the plug. Alternatively, the interlocking projection may be polygonal or elliptical in shape. Preferably, the interlocking projection is formed on the main body portion at a position on the upper or outer side of the constricted passage, at such a position that it is tightly gripped and anchored in the interlocking groove of the nesting piece when the nesting piece is coupled with the main body portion. For this purpose, the nesting piece is provided with an annular interlocking groove which is arranged and dimensioned to tightly grip the interlocking projection of the main body portion.

In this connection, in a case where an annular groove is formed around the nesting piece as an interlocking groove, the axial width of the annular groove, namely, the axial width of a space between wall portions which opposingly rise from the bottom of the annular interlocking groove should be smaller than the thickness of the interlocking projection to grip the interlocking projection tightly in a compressed state and to anchor the nesting piece immovably on the main body portion of the plug. Further, the diameter at the bottom of the annular interlocking groove should be made larger than the inside diameter of the interlocking projection in order to ensure higher stability of the nesting piece in the coupled state and tightness of hermetical seal between the main body portion and the nesting piece. When the nesting piece is coupled with the main body portion, pressure is exerted axially on the interlocking projection by the nesting piece to hold the interlocking projection in a resiliently compressed state. In so doing, there is no necessity for applying pressure on the entire engaging surfaces of the interlocking projection. For instance, a compressible protuberance, preferably a compressible annular ridge can be provided on one side of the interlocking projection.

When no instrument is inserted, meeting edges of the slit in the nesting piece should be retained in a tightly closed state. In a case where the diameter at the bottom of the annular interlocking groove is made larger than the inside diameter of the interlocking projection as mentioned hereinbefore, the meeting edges of the slit which is located on the inner side of the annular interlocking groove are constantly urged into a tightly closed position under pressure which is exerted from outside by the interlocking projection.

The above and other objects, features and advantages of the present invention will become apparent from the following description of preferred embodiments, taken in conjunction with the accompanying drawings. Needless to say, the present invention should not be construed as being limited to the particular forms which are shown in the drawings by way of example.

BRIEF DESCRIPTION OF THE DRAWINGS

In the accompanying drawings:

FIG. 2 a sectional view taken through an instrument entrance leading to an endoscopic biopsy channel, having a valved plug according to the present invention fitted in an inlet opening of the instrument entrance;

DESCRIPTION OF PREFERRED EMBODIMENTS

Figure 1:
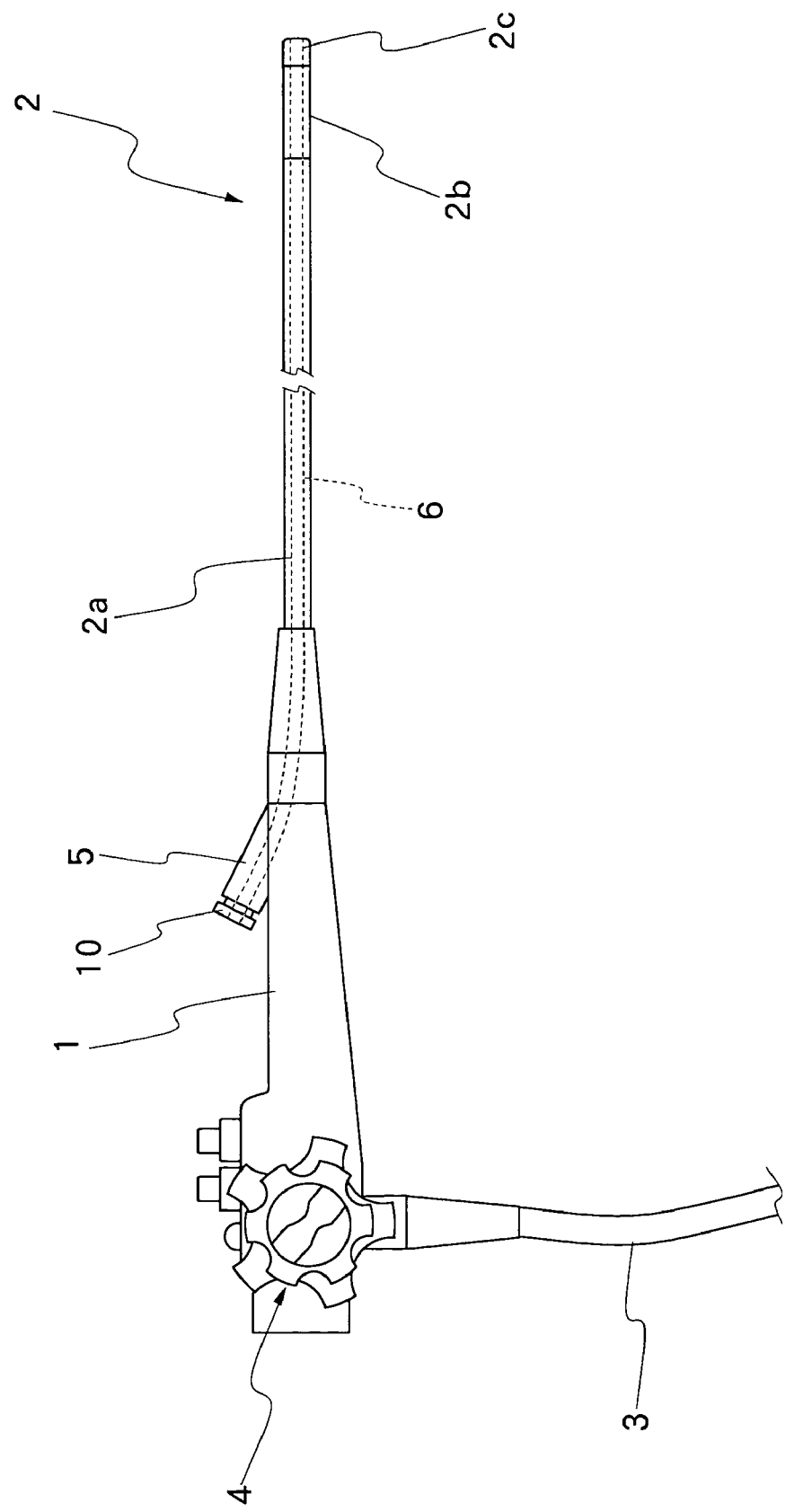
FIG. 1 is a schematic illustration of an endoscope employing a valved plug according to the present invention.

Hereafter, the present invention is described more particularly by way of its preferred embodiments with reference to the accompanying drawings. Shown in FIG. 1 is the general layout of an endoscope. In that figure, indicated at 1 is a manipulating head assembly of the endoscope, at 2 an elongated insertion tube, and at 3 a universal cable. The insertion tube 2 which is extended out on the front side of the manipulating head assembly 1 is composed of an elongated flexible body 2a which occupies a major portion of the elongated insertion tube 2 and flexibly bendable along bent portions in a path of insertion, a rigid tip end section 2c and an angle section 2b which is connected between a fore distal end of the flexible body portion 2a and the rigid tip end section 2c. Illumination means as well as optical image pickup means of endoscopic observation means (both not shown) are built into a casing of the rigid tip end section 2c of the insertion tube 2. The angle section 2b can be bent into an arbitrary direction by remote control angulation means for the purpose of guiding the rigid tip end section 2c along a bent path of insertion or for changing the view field of the endoscopic observation means on the rigid tip end section 2c. Angulation of the angle section 2b is maneuvered by remote control from an angulation control means 4 which is provided on the manipulating head assembly 1.

The endoscope is usually arranged to permit not only observation of an intracavitary portion of interest through the above-mentioned endoscopic observation means but also a treatment to and sampling of tissues from a spotted diseased portion. For this purpose, an entrance 5 to a biopsy channel 6 is provided on the casing of the manipulating head assembly 1, permitting to insert a biopsy or surgical instrument into the biopsy channel 6 which extends from the biopsy channel entrance passage 5 to the fore end of the rigid tip end section 2c. The fore end of the biopsy channel 6 is opened in the casing of the rigid tip end section 2c along with illumination windows and an observation window of the endoscopic observation means. Whenever necessity arises, forceps or other biopsy or surgical instrument can be inserted into the biopsy channel 6 through the instrument entrance 5 on the manipulating head assembly 1 and projected into a body cavity through a biopsy channel outlet opening on the rigid tip end section 2c at the distal end of the insertion tube 2.

Further, in many cases the biopsy channel 6 is also utilized as a suction passage. Therefore, although not shown in the drawings, the biopsy channel 6 is divided into two branch passages within the casing of the manipulating head assembly 1, one branch passage leading to the instrument entrance 5 and the other branch passage leading to a passage to be connected to an aspirator through the manipulating head assembly 1 and the universal cable 3. Further, a suction valve is provided on the manipulating head assembly 1 thereby to bring the biopsy channel 6 into and out of communication with an aspirator.

In case body fluid or other smudging fluids exist in a body cavity under endoscopic observation, the suction valve is operated to evacuate such fluids into the suction passage to better the visibility of an intracavitary site under endoscopic observation. If a diseased portion is spotted by an examination under better conditions, forceps or other instrument is inserted into the biopsy channel 6 and projected into the body cavity for treatment of the diseased portion, if necessary.

Therefore, the instrument entrance 5 which leads to the biopsy channel 6 needs to be maintained in a hermetically closed state, for example, at least during aspiration of body fluids, while permitting insertion of a treating instrument even in the hermetically closed state. Furthermore, after use, the interior of the biopsy channel 6 which has been contaminated with body fluids needs to be washed clean and disinfected. Accordingly, a plug 10 which is detachably fitted in an inlet opening of the instrument entrance 5 is arranged to maintain the inlet opening normally in a hermetically closed state while permitting insertion of an instrument even in the hermetically closed state.

The construction of the valved plug 10 according to the present invention is shown more particularly in FIG. 2. In this figure, indicated at 11 in that figure is a branch passage which is connected to an instrument entrance way or passage 12 and, although not shown in the drawings, provided with joint portions for connection to the biopsy channel 6 and a suction passage. A mouth piece 13 is provided at the outer end of the instrument entrance passage 12, and the plug 10 is fitted on the mouth piece 13 which is so shaped as to releasably hold the plug 10 thereon. More specifically, the tubular mouth piece 13 is provided with an annular groove 14 behind a bulged rim portion 15 which is formed around the outer open end of the mouth piece 13 for anchoring the plug 10 thereon.

Figure 3:
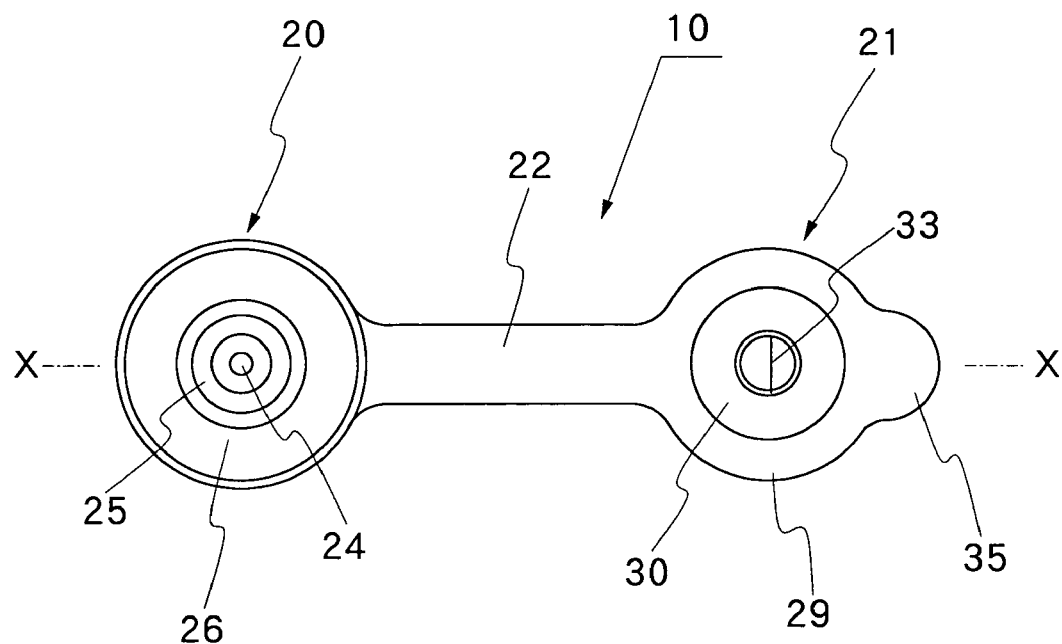
FIG. 3 is a plan view of the plug of FIG. 2, having a valved nesting piece of the plug uncoupled and separated from a main body portion of the plug.
Figure 4:
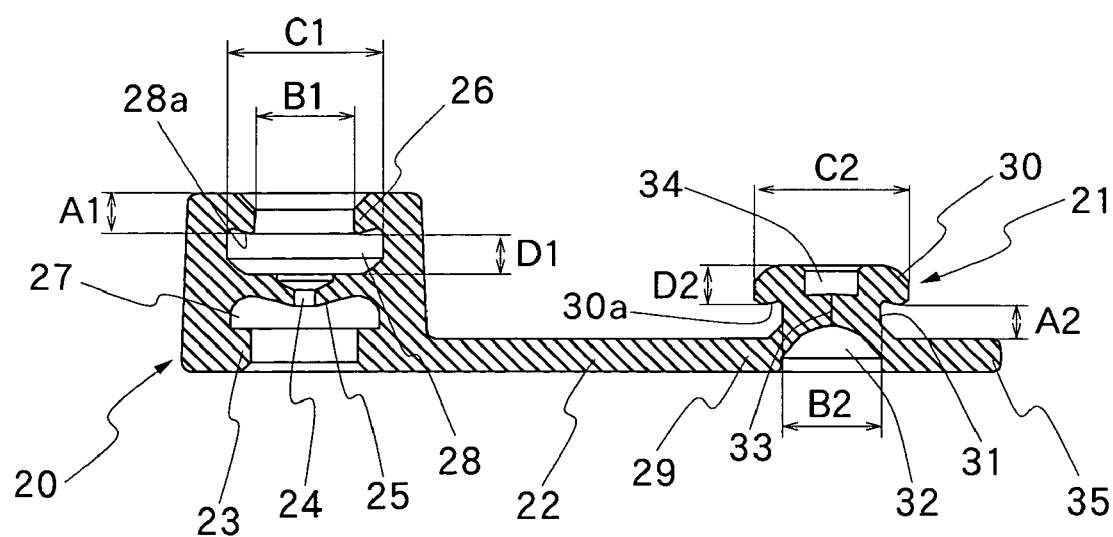
FIG. 4 is a sectional view taken in the direction of arrows X—X in FIG. 3.

Further, the plug 10 is shown in plan and sectional views in FIGS. 3 and 4, respectively. As seen in these figures, the plug 10 is formed of resilient material like rubber in its entirety and composed of a tubular main body portion 20 and a valved nesting piece 21, which are integrally formed at the opposite ends of a flat flexibly foldable connector strip 22.

The main body 20 of the plug 10 is formed generally in a round tubular shape on the outer peripheral side, and internally provided with a first inward projection in the form of an annular ledge 23 which is projected radially inward from one axial end to be fitted on the mouth piece 13 of the instrument entrance way 12. A partition wall 25 is formed across an axially intermediate portion of the main body 20, and a constricted passage 24 is provided at the center of the partition wall 25. Further, as an interlocking projection, the main body portion 20 is provided with a second inward projection in the form of an annular ledge 26 which is projected radially inward at the other outer end away from the first annular ledge 23. A first annular groove 27 is formed between the first annular ledge 23 and the partition wall 25, and a second annular groove 28 is formed between the partition wall 25 and the second annular ledge 26. Further, the valved nesting piece 21 is composed of a hemispherical cup-like body portion 29, and an annular flange portion 30 formed integrally on top of the hemispherical body portion 29 in such a way that it rises and then spread and bulged in a radially outward direction to hang over the circumference of the hemispherical body portion 29. An annular groove 31 is formed between the flange portion 30 and the hemispherical body 29. Rising wall portions at the opposite sides of the annular groove 31 forms interlocking wall portions which are brought into interlocking engagement with the second annular ledge portion 26 on the main body portion 20 to hold the latter securely in position. A concavely hemispherical instrument guide surface 32 is provided on the hemispherical body portion 29 of the valved nesting piece 21 on the side away from the annular flange portion 30. A slit 33 is provided at the bottom of the concavely hemispherical instrument guide surface 32. A hollow cavity 34 is provided under the slit 33, that is to say, on the side away from the concavely hemispherical instrument guide surface 32. This hollow cavity 34 allows easy inward deformations of slit portions when an instrument is inserted into the plug, and at the same time it can serve for adjustments of the wall thickness of the top portion of the hemispherical body portion 29 with the slit 33.

The outside diameter of the main body portion 20 of the plug is substantially same as that of the valved nesting piece 21. For use in coupling and uncoupling the valved nesting piece 21 with and from the main body 20 of the plug, a gripping tab 35 is extended out from the valved nesting piece 21 on the opposite side away from the foldable connecting strip 22.

Being arranged in the manner as described above, various portions of the main body 20 and valved nesting piece 21 of the plug 10 are held in particular dimensional relations as described below with reference to FIG. 4. Firstly, the first annular groove 27 on the main body portion 20 is fitted on the anchor rim portion 15 of the mouth piece 13, while the first annular ledge 23 is fitted in the annular groove 14 to detachably fit the plug 10 on the mouth piece 13 of the instrument entrance way 12. Besides, for coupling and uncoupling the valved nesting piece 21 with and from the main body portion 20 of the plug 10 on the mouth piece 13 of the instrument entrance as described later on, the coupling strength between the main body portion 20 and the mouth piece 13 should be stronger than the coupling strength between the valved nesting piece 21 and the main body portion 20. Therefore, relative to the annular groove 13 and the anchor rim portion 15 of the mouth piece 13, the first annular ledge 23 and the first annular groove 27 on main body portion 20 of the plug 10 are arranged to have relatively large differences in dimension, so that the first annular ledge 23 and the first annular groove 27 of the main body portion 20 of the plug 10 undergo compressive deformation to relatively large degree when the main body portion 20 is fitted on the mouth piece 13.

After fitting the main body portion 20 of the plug 10 on the mouth piece 13 of the instrument entrance way 12 in the manner as described above, the valve nesting piece 21 is coupled with the main body portion 20. At this time, the second annular ledge 26 which constitutes an interlocking member on the part of the main body portion 20 is gripped between the hemispherical body portion 29 and confronting radial wall portion 30a on the lower side of the flange portion 30 to connect the valved nesting piece 21 securely to the main body portion 20 of the plug 10.

In order to increase the coupling strength between the main body portion 20 and the valved nesting piece 21, the second annular ledge 26 is arranged to have a thickness A1 which is larger than a width A2 of the annular groove 31 which is formed between the hemispherical body portion 29 and the radial wall surface 30a on the lower side of the flange portion 30 of the valved nesting piece 21. Accordingly, when coupled with the valved nesting piece 21, the second annular ledge 26 on the main body portion 20 is compressed to a certain degree. Further, the second annular ledge 26 of the main body portion 20 is arranged to have an inside diameter B1 which is smaller than an outside diameter B2 at the bottom of the annular groove 31 on the valved nesting piece 21. As a consequence, the second annular ledge 26 on the main body portion 20 subjected to a biasing force which tends to spread the second annular ledge 26 in a radially outward direction. However, the second annular groove 28 on the main body portion 20 is arranged to have an inside diameter C1 which is either larger than or equivalent with an outside diameter C2 flange portion 30 of the nesting piece 21. Further, the second annular groove 28 on the main body portion 20 is arranged to have a diameter D1 which is larger than a thickness of the flange portion 30 of the nesting piece 21.

For setting the plug 10 at the instrument entrance 5, the first annular ledge 23 of the main body portion 20 is pushed onto and fitted on the anchor rim portion 15 of the mouth piece 13. Since the plug 10 as a whole is made of a resilient material, the first annular ledge portion 23 can be spread to a larger diameter through elastic deformation and fitted into the annular groove 14 of the mouth piece 13 riding over the anchor rim 15. As a consequence, the main body portion 20 of the plug 10 is fixedly set at the instrument entrance 5.

Figure 5:
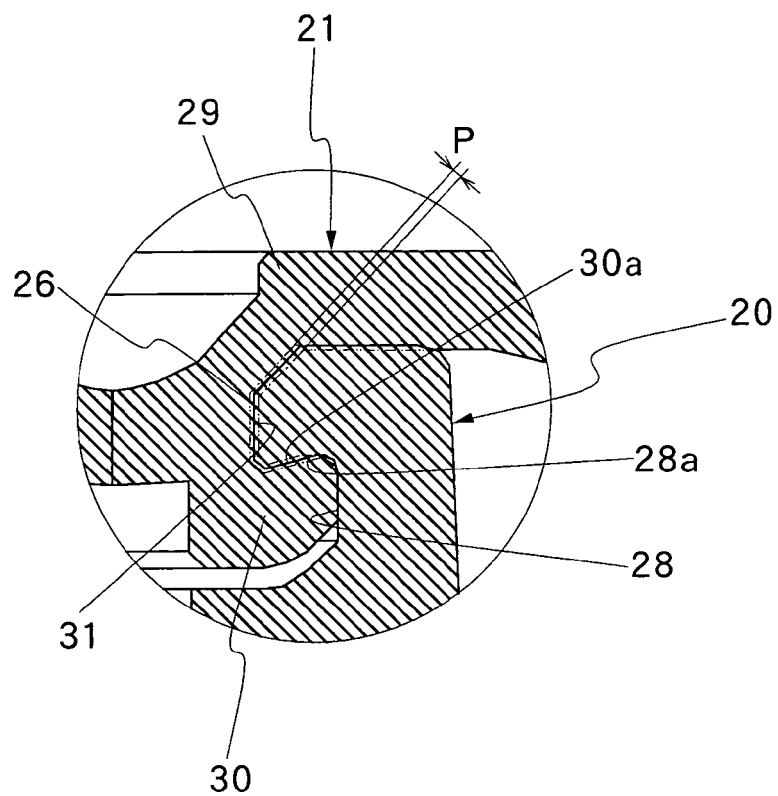
FIG. 5 is a fragmentary sectional view showing part of the plug of FIG. 2 on an enlarged scale.

In the next place, the valved nesting piece 21 is coupled with the main body portion 20. This can be done by bending the foldable connecting strip 22 into U-shape and pushing the flange portion 30 of the nesting piece 21 toward the lower side of the second annular ledge 26 of the body portion 20. By so doing, the second annular ledge 26 is spread in diameter while the flange portion 30 of the nesting piece 21 is compressed to a smaller diameter. Then, the flange portion 30 of the nesting piece 21 is pushed in to ride over the second annular ledge 26 and accommodated in the second annular groove 28 of the main body portion. In this state, as shown in FIG. 5, the second annular ledge 26 on the main body portion 20 and the flange portion 30 of the nesting piece 21 are compressed to a degree P relative to each other. As a result of this relative compressing interference, the nesting piece 21 is coupled with the main body portion 20 of the plug 10 tightly in good conditions in terms of hermetical tightness.

In an elastically deformed state, the second annular ledge 26 of the main body portion 20 is gripped from its upper and lower sides between a base portion of the hemispherical body 29 and the flange portion 30. Besides, the second annular ledge 26 is compressed in a radially outward direction by the annular groove 31 of the valved nesting piece 21. Accordingly, once coupled with the main body portion 20, the valved nesting piece 21 is retained in a fixed state substantially as one unitary structure and locked against movements relative to the main body portion 20 not only in the axial direction of the biopsy channel 6 but also in radial directions perpendicular to the longitudinal axis of the instrument entrance way 12. Accordingly, the valved nesting piece 21 is retained in an immovable state relative to the main body portion 20 of the plug even if a large pressure is applied to interior portions of the plug 10 by insertion of various treating instruments into the biopsy channel 5 through the slit 33 in the nesting piece 21 and the constricted passage 24 on the main body portion 20 of the plug 10.

As a consequence, even if an instrument which is stiff and large in outside diameter like forceps is inserted into the biopsy channel 6 and then abruptly extracted out of the instrument entrance 5 or even if a suction valve is closed after aspiration, no relative movements occur to the nesting piece 21 and the main body portion 20 of the plug 10, with the second annular ledge 26 and the annular groove 31 in fitting engagement with each other always in a stabilized state. Accordingly, there is little possibility of coupling portions of the plug being deformed by repeated insertion and extraction of instruments, that is to say, there is little possibility of the nesting piece 21 being forcibly uncoupled from the main body portion 21 during use. As mentioned hereinbefore, abrupt extraction of an instrument out of the instrument entrance 5 can result in exertion on the plug 10 of a force which acts to separate the nesting piece 21 forcibly from the main body portion 20. In order to enhance the coupling strength between the second annular ledge 26 and the annular groove 31 of the nesting piece 21 against a separating force, it is desirable to taper engaging surfaces 30a and 23a of the flange portion 30 and the second annular ledge 26 in wedge-like shapes, inclined upward in radially outward and inward directions respectively, so that they are wedged into each other when an axial separating force is exerted thereto. A relatively shallow taper angle suffices for this purpose. An unduly large tape angle will make it difficult to separate the valved nesting piece 21 from the main body portion 20 of the plug 10.

For insertion of a soft and non-stiff instrument like a pliable rubber tube, it may become necessary to open the valved nesting piece 21 to place the tube directly into the throttle passage 24 instead of passing same through the slit 33. In such a case, the nesting piece 21 can be separated from the main body portion 20 simply by pulling tab portion 35 of the nesting piece 21 upward. Partly because the hollow cavity 34 is provided on the inner side of the flange portion 30 of the nesting piece 21 and partly because the second annular groove 28 is formed in a larger width as compared with the thickness of the flange portion 30 of the nesting piece 21 to leave a gap space of a certain width beneath the flange portion 30, the flange portion 30 is deformed in inward directions in the local regions in the vicinity of the tab portion 35 to permit separation of the nesting piece 21 from the main body portion 20 without difficulties.

In this instance, when the plug 10 is fitted on the mouth piece 13 of the instrument inlet opening 12, meeting edge portions of the slit 33 on the nesting piece 21 should be closed tightly to each other. The slit 33 is formed at a position on the inner side annular groove 31, in which the second annular ledge 26 is fitted when the nesting piece 21 is coupled with the main body portion 20. Since the second annular ledge 26 is arranged to have an inside diameter B1 which is smaller than the diameter B2 at the bottom of the annular groove 31, the slit 33 is pushed by the second annular ledge 26 from outside and thereby the meeting edges of the slit 33 are maintained in a tightly pressed state relative to each other. Therefore, the nesting piece 21 is coupled with the main body portion 20 in an advantageous manner for maintaining hermetical tightness of the slit 33 when no instrument is inserted in the biopsy channel 5.

Figure 6:
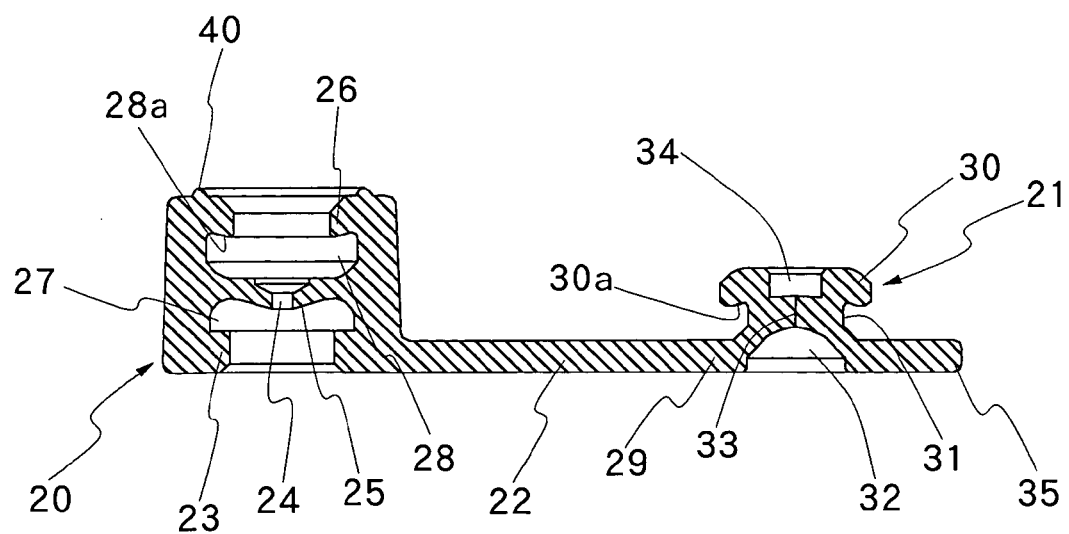
FIG. 6 is a sectional view similar to FIG. 4 but showing another embodiment of the valved plug according to the present invention.

In this connection, when the second annular ledge 26 on the main body portion 20 is gripped in an elastically deformed state between the hemispherical body portion 29 and flange portion 30 of the valved nesting piece 21, it is important to hold the hemispherical body portion 29 and the second annular ledge 26 in abutting engagement with each other over the entire joining surface areas. For example, in a modification shown in FIG. 6, an annular ridge 40 is formed on top of the second annular ledge 26 of the main body portion 20. As the valved nesting piece 21 is coupled with the main body portion 20, the annular ridge 40 is deformed by compression to enhance the above-mentioned gripping function. Accordingly, in this case, the thickness of the second annular ledge 26 is increased by addition of the annular ridge 40, so that the thickness of the second annular ledge 26 itself may be same as or smaller than the width of the annular groove 31.

What is claimed is:

1. In a valved plug to be fitted on a mouth piece at an inlet opening of an instrument entrance passage leading to a biopsy channel of an endoscopic insertion tube, said plug being formed of a resilient material in its entirety and having, at opposite ends of a foldable connecting strip, a generally tubular main body portion internally formed with a constricted passage of a smaller diameter as compared with said inlet opening of said instrument entrance passage, in a radial partition wall located at an intermediate portion between outer and inner ends thereof, and a nesting piece adapted to be detachably coupled with said main body portion and having a normally closed slit valve in axial alignment with said constricted passage in said main body portion to permit insertion of an instrument therethrough:

an annular inward interlocking projection provided at an outer end of said main body portion to be coupled with said nesting piece, said interlocking projection being axially spaced from said radial partition wall by an internal annular groove formed around an inner periphery of said main body portion;

said slit valve provided in a circular fitting body portion of said nesting piece to be fitted in said main body portion;

an annular interlocking groove formed around an outer periphery of said fitting body portion of said nesting piece on an outer side of an annular interlocking flange provided at an innermost end of said fitting body portion;

said annular interlocking projection on said main body portion having a thickness greater than an axial width of said annular interlocking groove on said fitting body portion of said nesting piece, and an inside diameter smaller than a root diameter of said annular interlocking groove on said fitting body portion, to hold said annular interlocking projection in a compressed state by a bottom surface and riser wall portions of said annular interlocking groove when said nesting piece is coupled with said main body portion; and said internal annular groove having a larger axial width than said annular interlocking flange on said fitting body portion to leave a free space between said radial partition wall on said main body portion and said fitting body portion of said nesting piece to permit easy inward deformation of said slit valve toward said constricted passage when opened by insertion of an instrument.

2. A valved plug as defined in claim 1, wherein said main body portion of said plug is provided with an annular ledge at an inner end to be fitted on an anchor rim of said mouth piece.

3. A valved plug as defined in claim 1, wherein said nesting piece is provided with a concavely hemispherical instrument guide surface on an outer side to guide an instrument toward said slit valve.

4. A valved plug as defined in claim 3, wherein said circular fitting body portion of said nesting piece is provided with a hollow cavity centrally of said annular interlocking flange immediately on the inner side of said slit valve facing said free space.

5. A valve plug as defined in claim 4, wherein said slit valve is formed in a thin wall portion between said hemispherical instrument guide surface and said hollow cavity of said nesting piece.

6. A valve plug as defined in claim 5, wherein said thin wall portion is formed inward of said annular interlocking groove on the outer periphery of said fitting body portion of said nesting piece, biasing said slit valve toward a closed position by said annular interlocking projection which is in pressed engagement with said annular interlocking groove.

* * * * *